(12) United States Patent
McMillan

(10) Patent No.: US 9,050,097 B1
(45) Date of Patent: Jun. 9, 2015

(54) METHOD AND DEVICE FOR SINGLE-POINT IDENTIFICATION OF NEURAL TISSUE DURING ENDOSCOPIC MICRODISCECTOMY

(76) Inventor: Marion R. McMillan, Seneca, SC (US)

( * ) Notice: Subject to any disclaimer, the term of this patent is extended or adjusted under 35 U.S.C. 154(b) by 305 days.

(21) Appl. No.: 13/476,572

(22) Filed: May 21, 2012

Related U.S. Application Data

(60) Provisional application No. 61/488,359, filed on May 20, 2011.

(51) Int. Cl.
*A61B 18/18* (2006.01)
*A61B 18/14* (2006.01)

(52) U.S. Cl.
CPC .................................. *A61B 18/1402* (2013.01)

(58) Field of Classification Search
CPC ...................... A61N 1/0551; A61B 2018/0044
USPC ............................................................ 606/42
See application file for complete search history.

(56) References Cited

U.S. PATENT DOCUMENTS 6,135,999 A * 10/2000 Fanton et al. ................... 606/45

* cited by examiner

*Primary Examiner* — George Manuel
(74) *Attorney, Agent, or Firm* — Sara C. Kanos; Nexsen Pruet, LLC

(57) ABSTRACT

A method and device for single-point identification of neural tissue during endoscopic spinal surgery including the use of an electrical switch that accepts separate inputs from a bipolar generator and an electrical nerve stimulator.

18 Claims, 3 Drawing Sheets

METHOD AND DEVICE FOR SINGLE-POINT IDENTIFICATION OF NEURAL TISSUE DURING ENDOSCOPIC MICRODISCECTOMY

CROSS REFERENCE TO RELATED APPLICATIONS

This application claims priority to U.S. Provisional Patent Application No. 61/488,359 filed May 20, 2011, which is incorporated herein by reference.

BACKGROUND

The present invention relates generally to endoscopic spinal surgery, microdiscectomy, and to the identification of neural tissue during these procedures. More particularly, the present invention is directed to a switching device used to alternatively allow bipolar surgical dissection or produce nerve stimulation using a single surgical instrument through the working channel of the endoscope without the need to introduce or exchange additional instruments.

Minimally invasive spinal surgery has greatly increased the convenience and safety of treatment of common painful spinal conditions. Endoscopic microdiscectomy with or without foraminotomy is one such approach to the treatment of herniated disc and spinal stenosis utilizing small tubular retractor instrument systems and high resolution digital video endoscopes to access and treat soft tissue and bony pathology within the spinal canal with minimal tissue trauma associated with the procedure.

Current generation spinal endoscopes are equipped with "working channels" that allow the placement of operating instruments within the diameter of the endoscope itself, thus limiting the size of the entire surgical access window to a single portal, typically 7-10 mm in diameter. The ability to place all operating instruments through the working channel further complements the essential goals of minimal tissue trauma for operating efficiency, safety, reduced operating time, and fewer surgical complications.

In endoscopic spinal surgery, rapid and reliable identification of neural tissue is essential to safe practice. The clinical use of sensory and motor nerve stimulation has become a mainstay of current open spinal surgery and endoscopic surgical practice by a variety of methods. Existing methods of neural monitoring during spine surgery such as elaborate EMG and SSEP devices require that nerve injury be imminent or actual as a condition of detection. Direct electrical stimulation of a suspected neural structure, however, is a proven method of prospective neural identification without threatened or actual injury to the nerve. Thus, the ability to provide direct electrical stimulation to suspected neural structure while performing minimally invasive endoscopic surgery would be highly beneficial and especially beneficial during physician training or proctoring to help shorten the learning curve and decrease the potential for patient injury while developing experience with endoscopic techniques. In addition, when performing procedures on awake or lightly sedated verbally responsive patients, symptoms referable to a specific neural territory may be confirmed during surgery to further confirm surgical treatment efficacy.

Accordingly, there is a need for a device and method for providing direct atraumatic identification of neural tissue by electrical stimulation through the working channel of the spinal endoscope.

SUMMARY

The following presents a simplified summary of the invention in order to provide a basic understanding of some aspects of the invention. This summary is not an extensive overview of the invention. It is not intended to identify key or critical elements of the invention or to delineate the scope of the invention; its sole purpose is to present concepts of the invention in a simplified form as a prelude to the more detailed description that is subsequently presented.

In one embodiment of the present invention, the invention includes a device for single-point identification of neural tissue during endoscopic spinal surgery. The device includes a solid state electronic switch and means for controlling a functional electrical circuit to independently provide surgical bipolar dissection and nerve stimulation by a single surgical instrument. The electronic switch is connected to a surgical bipolar generator and an electrical nerve stimulator so that the switch accepts separate electrical inputs from said surgical bipolar generator and said electrical nerve stimulator.

In an alternative embodiment of the present invention, the device for single-point identification of neural tissue during endoscopic spinal surgery, includes a neural tissue detector device having a switch electrically connected to a first input port, a second input port, and a third input port. A nerve stimulator is electrically connected to the first input port, a bipolar generator is electrically connected to the second input port, and a surgical instrument is electrically connected to the third input port. When the switch is in a first position, the surgical instrument is controlled by the nerve stimulator and when the switch is in a second position, the surgical instrument is controlled by the bipolar generator.

In another embodiment of the present invention, the invention includes a method for single-point identification of neural tissue during endoscopic spinal surgery. The method includes providing a device for single-point identification of neural tissue during endoscopic spinal surgery. The device includes a solid state electronic switch and means for controlling a functional electrical circuit to independently provide dissection and nerve stimulation by a single surgical instrument. The electronic switch is connected to a surgical bipolar generator and an electrical nerve stimulator so that the switch accepts separate electrical inputs from said surgical bipolar generator and said electrical nerve stimulator. The method further includes identifying neural tissue employing the device.

Other features and their advantages will be readily apparent to those skilled in decorative arts, techniques and equipment from a careful reading of the Description of Representative Embodiments, accompanied by the following drawings.

DESCRIPTION OF REPRESENTATIVE EMBODIMENTS

The present invention is related to a device and method that is particularly suitable for single-point identification of neural tissue during endoscopic microdiscectomy. More particularly, the present invention is directed to a device and method of performing endoscopic spinal surgery, which allows for surgical dissection and electrical nerve stimulation to be performed through a single surgical instrument designed and developed to be used through the working channel of a surgical endoscope, tubular retractor, or directly into an open surgical field. The unique design, features, and steps of the neural tissue detector device and method for using same preferably allows for electrical confirmation of appropriate tissue contact for dissection or nerve stimulation during surgical procedures and particularly endoscopic microdiscectomy. Although primarily described herein in terms of its use with endoscopic microdiscectomy and endoscopic spinal surgery, it will be clear that the device and method of the present invention may also be used in connection with a variety of other surgical procedures. The invention will be described with reference to the figures forming an integral non-limiting part of the instant specification. Throughout the description, similar elements will be numbered accordingly.

Figure 1:
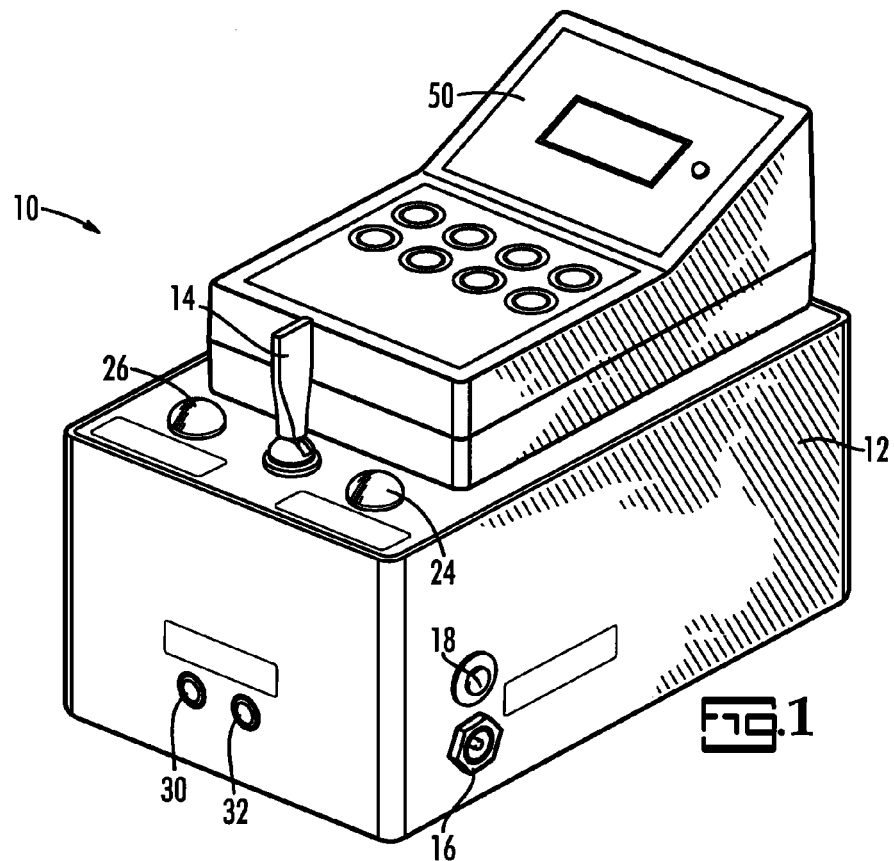
FIG. 1 illustrates a perspective view of the front and side of an embodiment of the device of the present invention.
Figure 2:
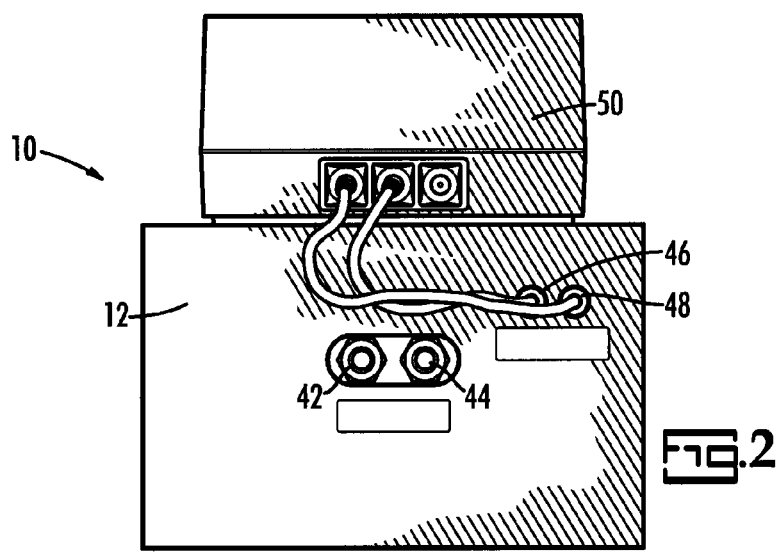
FIG. 2 illustrates a rear view of an embodiment of the device of the present invention.

FIGS. 1 and 2 disclose an embodiment of the neural tissue detector device 10 of the present invention. The embodiment of the neural tissue detector device 10 of FIGS. 1 and 2 includes a housing 12 encasing several electrically connected components, such as a solid state electronic switch, battery powered relays, and light emitting diodes (LED's). The components are preferably electrically connected to mechanisms and devices, such as shown in FIG. 3 and discussed more thoroughly below, to allow a single surgical instrument to have the capability of separately providing electrical current nerve stimulation and radiofrequency tissue ablation and removal during surgery.

As shown in FIG. 1, a switch 14, such as a double polar double throw (DPDT) toggle switch, may be provided on the upper surface of housing 12. Power may be supplied through power port 16 positioned on the side of the housing 12. In one embodiment, power is provided from a standard power outlet to a power port 16 of the detector device. When power is provided directly from a standard power outlet, an adaptor that converts the current to direct current (DC) with an input of approximately 12 volts may be incorporated. In an alternative embodiment, power is provided by a battery electrically connected to the detector device at power port 16. When power is supplied to power port 16, a first indicator signal 18, such as a LED, may appear indicating the existence of a completed electrical circuit and confirmation that the detector device is operable for use to detect appropriate tissue contact for dissection or nerve stimulation.

As shown in the embodiment disclosed in FIG. 1, the detector device includes two patient output ports 30 and 32. As shown in FIG. 3, a coupling attachment or plug 34 affixed to an electrical wire 36 may be inserted into output ports 30 and 32. At the opposing end of the electrical wire 36 is a surgical instrument, such as a bipolar surgical dissector 40, which may be inserted into the working channel of an endoscope, other surgical tubular retractor, or directly into the open surgical field for performing endoscopic or open spinal surgical dissection. The bipolar surgical dissector 40 preferably delivers surgical electrical current through bipolar electrodes for procedures such as cutting, ablation, vaporization, coagulation, and modulation of tissue. When used in connection with the present invention and placed in contact with neural tissue, the bipolar electrodes of the dissector 40 may also be used to conduct electrical stimulation impulses to produce sensory and/or motor responses for the clinical identification of suspected neural tissue.

Figure 3:
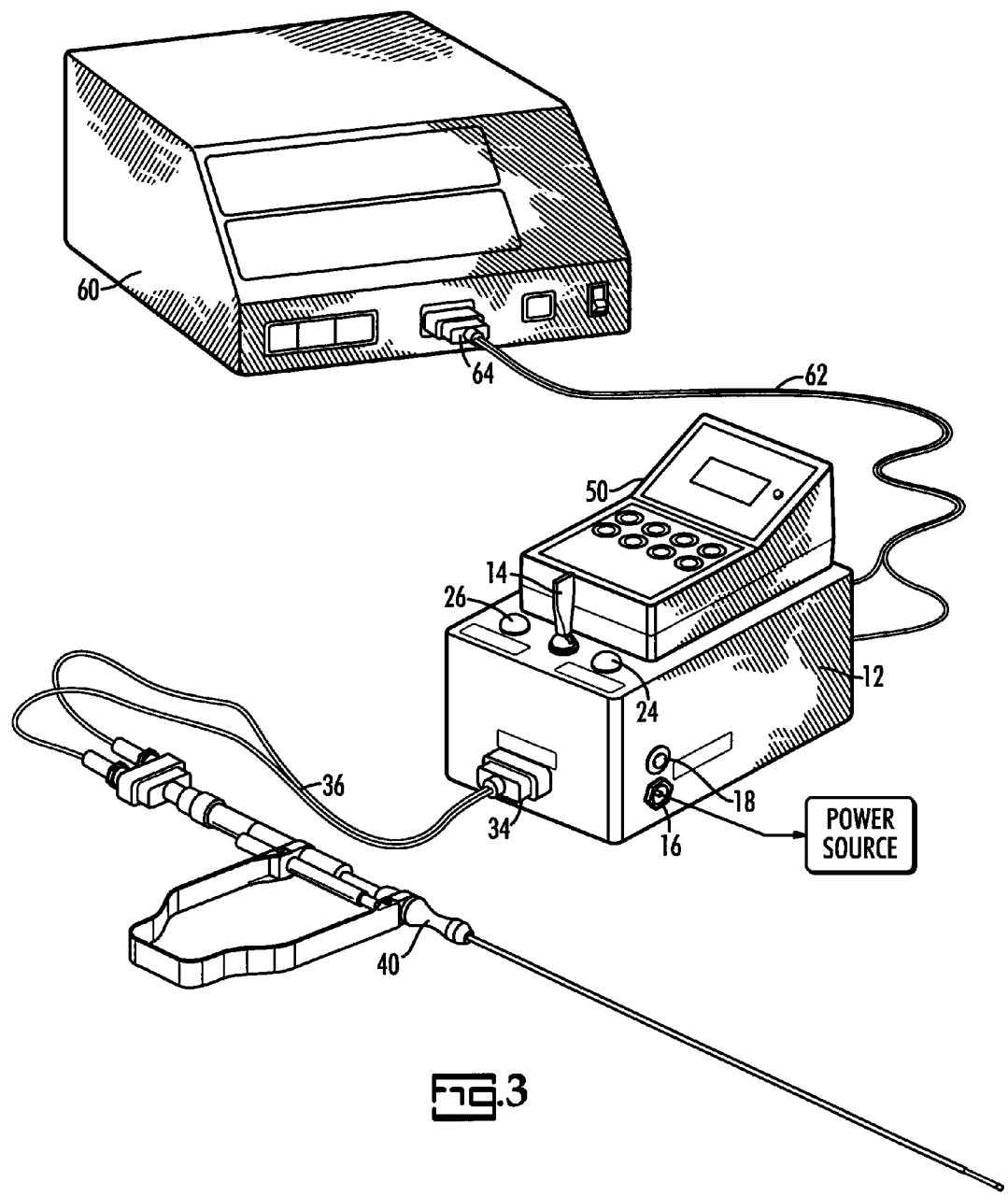
FIG. 3 illustrates a perspective view of an embodiment of the device of the present invention.

In the embodiment of FIGS. 1, 2, and 3, separate isolated electrical inputs are provided for an electrical nerve stimulator 50 and a surgical bipolar generator 60. It will be understood, however, that it is not necessary for both mechanisms 50 and 60 to be used during a surgical procedure and the use of either mechanism 50 and 60 depends on the needs of a particular surgeon during a particular surgical procedure involved. In the embodiment of FIG. 1, the nerve stimulator 50 is positioned on the upper surface of the housing 12 of the detector device 10. In the embodiment shown in FIG. 2, the nerve stimulator 34 is electrically wired to the detector device 10 via stimulator ports 46 and 48 positioned on the back side of housing 12.

In the embodiment of FIG. 2, two bipolar generator ports 42 and 44 are also included on the backside of housing 12 of detector device 10 for electrically connecting to a surgical bipolar generator, such as the bipolar generator 60 shown in FIG. 3. To electrically connect the surgical bipolar generator 60 to the detector device 10, a wire 62 having a plug 64 on one end may be inserted into the surgical bipolar generator 60 and the opposing end of wire 62 may have couplings for inserting into bipolar generator ports 42 and 44. In one embodiment, the surgical bipolar generator is a Surgitron device distributed by Elliquece, which typically distributes high frequency currents or radiofrequency to a bipolar dissector to perform dissection procedures such as cutting, ablation, vaporization, coagulation, and modulation of tissue.

The switch 14 controls whether the bipolar dissector 40 distributes bipolar electrical current, supplied by the surgical bipolar generator 60, or nerve stimulation current, supplied by the nerve stimulator 50. To distinguish which current is being supplied to the bipolar dissector 40, the detector device 10 of FIGS. 1 and 3 further includes a nerve stimulator indicator signal 24 and a bipolar generator indicator signal 26. In one embodiment the signals are LED's and are distinct colors. When the nerve stimulator LED is illuminated, the surgical bipolar dissector 40 is receiving input from the nerve simulator. When the bipolar generator LED is illuminated, the surgical bipolar dissector 40 is receiving input from the surgical bipolar generator. The respective LEDs may be labeled with the type of current being distributed and/or the mechanism supplying the current to the dissector 40.

Figure 4:
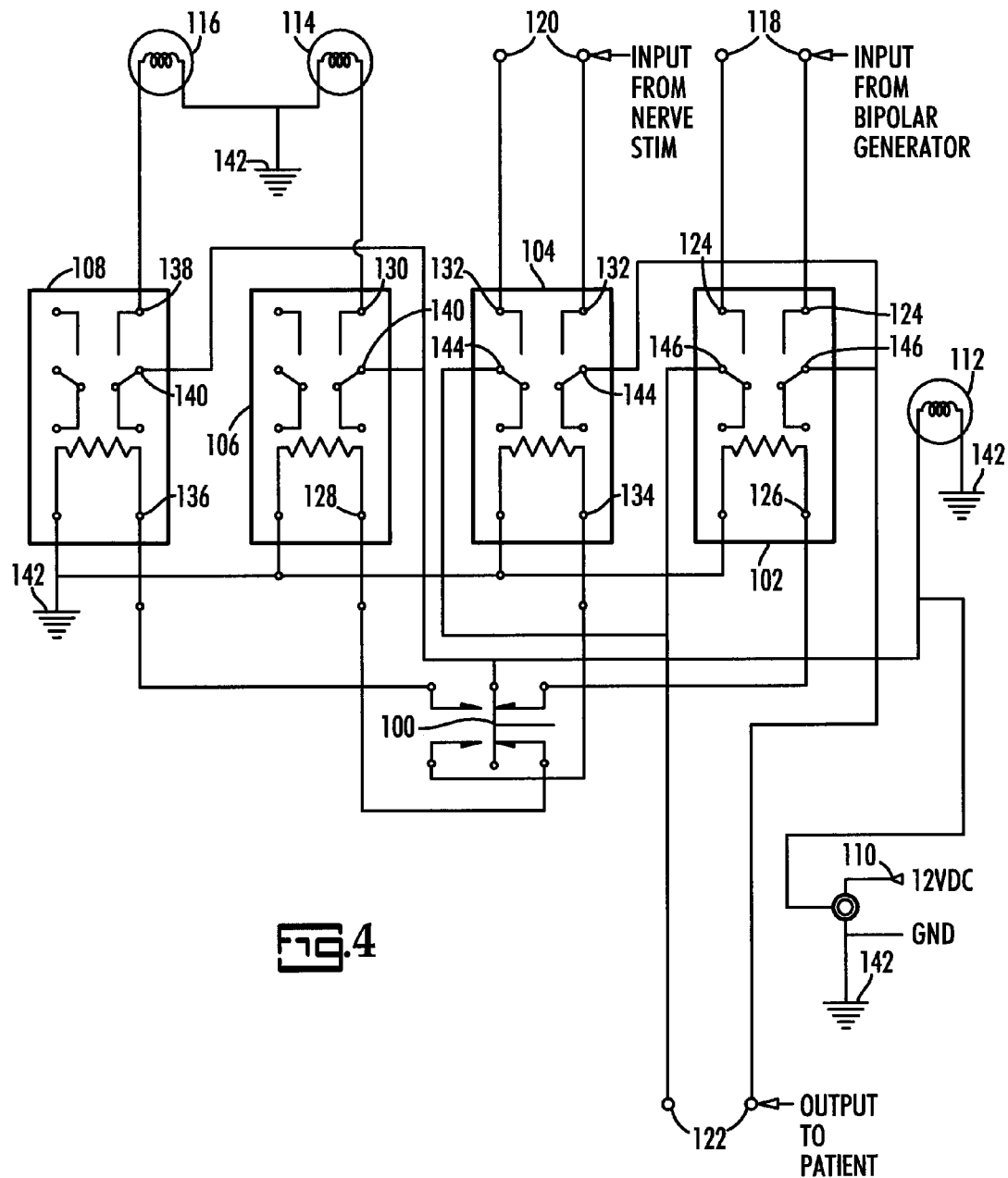
FIG. 4 includes a schematic view of the circuitry associated with an embodiment of the device of the present invention.

FIG. 4 discloses an example circuit diagram showing one technique for configuring an embodiment of the dissector device of the present invention. This embodiment incorporates a double polar double throw (DPDT) toggle switch 100, four relays 102, 104, 106, and 108, a power source 110, and three Light Emitting Diodes (LED's) 112, 114, and 116. A surgical bipolar generator at 118, such as generator 60 shown in FIG. 3, is electrically wired into relay 102 at 124. The toggle switch 100 is also electrically connected to relay 102 and relay 106 at 126 and 128, respectively. Relay 106 is further electrically connected to LED 114 at 130. A nerve stimulator at 120, such as stimulator 50 also shown in FIG. 3, is electrically wired into relay 104 at 132. The toggle switch 100 is also electrically connected to relay 104 and 108 at 134 and 136, respectively. Relay 108 is further electrically connected to LED 116 at 138. At 146 and 144, relays 102 and 104, respectively, are also electrically connected to a surgical bipolar dissector at 122, such as dissector 40 shown in FIG. 3.

Relays 106 and 108 are preferably connected to power source 110 at 140, such as a 12 volt direct current power supply. The power source 110 is connected to LED 112, which may be illuminated when power source 110 is electrically powered and connected. The detector device 10 and its components are also preferably grounded in appropriate locations such as shown in FIG. 4 at 142.

When toggle switch 100 is moved in a first direction to connect the circuit for the relays 102 and 106 electrically connected to a surgical bipolar generator device, LED 114 is illuminated and the bipolar surgical dissector electrically connected to the detector device at 122 receives input from the surgical bipolar generator. When receiving input from the surgical bipolar generator, the dissector delivers surgical electrical current through bipolar electrodes to perform dissection procedures such as cutting, ablation, vaporization, coagulation, and modulation of tissue. When the toggle switch 100 is moved in a second opposing direction, the surgical bipolar generator circuit is disconnected and the circuit associated with relays 104 and 108 is connected. LED 116 is illuminated and the bipolar surgical dissector electrically connected to the detector device at 122 is receiving input from the nerve stimulator. When receiving input from the nerve stimulator, electrical currents may be applied to the dissector to distinguish suspected neural tissue from non-neural bodily tissue. If the suspected neural tissue or an associated body part pulses or twitches in response to the electrical current supplied through the dissector, the suspected neural tissue is identified as a nerve.

The toggle switch 100 may be adjusted several times throughout an endoscopic surgical procedure. Therefore, instead of constantly interchanging separate tools into the endoscope, tubular retractor, or surgical field a first tool to supply nerve stimulation and a second to provide bipolar electrical current for dissection, a single dissector device may alternate between functions simply by the flip of a switch. The confirmation of bipolar electrical current and nerve stimulation current provided by the present invention increases surgical efficiency and reliability because only a single surgical instrument need be used for performing both functions. Moreover, electrical confirmation of the functional electrical integrity of the bipolar contacts is instrumental to successful operation of the invention to ensure that the bipolar contacts remain electrically intact and are not damaged or unknowingly rendered inoperative through internal heating, surgical trauma, or carbonization of the contacts during intraoperative use.

It will be understood that alternative forms and quantities of switches, signal indicators, ports, and components within the detector device may be utilized without departing from the spirit and the scope of the present invention. Furthermore, the positions and locations of the components of the detector device as well as the connections to and positions of the nerve stimulator and surgical bipolar generator are but one example of the possible configurations of the present invention. Varying voltage power supplies as well different types of power supplies are contemplated and may require the addition of a converter.

Further, it should be noted that there are several configurations suitable for the design of the detector device of the present invention, and the shapes, sizes, and dimensions of the parts of the detector device discussed above are for example only and represent but one of the configurations of the detector device. Other configurations altering the number of parts and components, attachment positions of the parts and components, means for attaching and securing the parts and components, and shapes, sizes, and dimensions of the parts and components could be employed to demonstrate the invention and are intended to be encompassed by the present invention. The description and drawings should not be deemed to narrow the scope of the present invention in any way.

While various embodiments of the present invention have been described above, it should be understood that they have been presented by way of example, and not limitation. It will be apparent to persons skilled in the relevant art(s) that various changes in form and detail can be made therein without departing from the spirit and scope of the present invention. In fact, after reading the above description, it will be apparent to one skilled in the relevant art(s) how to implement the invention in alternative embodiments. Thus, the present invention should not be limited by any of the above described exemplary embodiments.

In addition, it should be understood that the figures, which highlight the functionality and advantages of the present invention, are presented for purposes of example only. The architecture of the present invention is sufficiently flexible and configurable, such that it may be used in ways other than that shown in the accompanying figures.

Further, the purpose of the Abstract is to enable the U.S. Patent and Trademark Office and the public generally, and especially the scientists, engineers, and practitioners in the art who are not familiar with patent or legal terms or phraseology, to determine quickly from a cursory inspection the nature and essence of the technical disclosure of the application. The Abstract is not intended to be limiting as to the scope of the invention in any way.

What is claimed is:

1. A device for single-point identification of neural tissue during endoscopic spinal surgery, comprising:
    a solid state electronic switch and means for controlling a functional electrical circuit to independently provide surgical bipolar dissection and nerve stimulation by a single surgical instrument, wherein said electronic switch is connected to a surgical bipolar generator and an electrical nerve stimulator, wherein said switch accepts separate electrical inputs from said surgical bipolar generator and said electrical nerve stimulator, and wherein said switch is operatively connected to a first LED that is illuminated to indicate bipolar electrical current, a second LED that is illuminated to indicate nerve stimulation current, and a third LED that is illuminated to indicate the presence of a completed electrical circuit.

2. The device as recited in claim 1, wherein said surgical instrument is a bipolar surgical dissector.

3. The device as recited in claim 1, wherein said solid state electronic switch is a double polar double throw toggle switch.

4. The device as recited in claim 1, wherein said means for controlling a functional electrical circuit comprises a first relay electrically connected to said switch and said surgical bipolar generator and a second relay electrically connected to said switch and said electrical nerve stimulator.

5. The device as recited in claim 4, wherein said means for controlling a functional electrical circuit further comprises a third relay electrically connected to said switch and a first indicator signal, wherein when said switch accepts electrical input from said bipolar generator, said first indicator signal responds.

6. The device as recited in claim 5, wherein said means for controlling a functional electrical circuit further comprises a fourth relay electrically connected to said switch and a second indicator signal, wherein when said switch accepts electrical input from said nerve stimulator, said second indicator signal responds.

7. The device as recited in claim 6, wherein said third and fourth relays are electrically connected to a power source.

8. A method for single-point identification of neural tissue during endoscopic spinal surgery, comprising:
    providing the device as recited in claim 1; and
    identifying neural tissue employing said device.

9. The method as recited in claim 8, wherein said method further comprises dissecting bodily tissue employing said device.

10. The method as recited in claim 8, wherein said method further comprises positioning said switch to accept input from said surgical bipolar generator and positioning said switch to accept input from said electrical nerve stimulator.

11. A device for single-point identification of neural tissue during endoscopic spinal surgery, comprising:
- a neural tissue detector device having a switch electrically connected to a first input port, a second input port, and a third input port;
- a nerve stimulator electrically connected to said first input port;
- a bipolar generator electrically connected to said second input port; and
- a surgical instrument electrically connected to said third input port;
- wherein when said switch is in a first position, said surgical instrument is controlled by said nerve stimulator and wherein when said switch is in a second position, said surgical instrument is controlled by said bipolar generator.

12. The device as recited in claim 11, wherein said surgical instrument is a bipolar surgical dissector.

13. The device as recited in claim 11, wherein said neural tissue detector device further comprises an indicator signal for determining whether said surgical instrument is receiving input from said nerve stimulator or said bipolar generator.

14. The device as recited in claim 13, wherein said indicator signal includes a first light emitting diode, which is illuminated when said surgical instrument is receiving input from said nerve stimulator.

15. The device as recited in claim 14, wherein said indicator signal includes a second light emitting diode, which is illuminated when said surgical instrument is receiving input from said bipolar generator.

16. A method for single-point identification of neural tissue during endoscopic spinal surgery, comprising:
- providing the device as recited in claim 11; and
- identifying neural tissue employing said device.

17. The method as recited in claim 16, wherein said method further comprises dissecting bodily tissue employing said device.

18. The method as recited in claim 17, wherein said method further comprises positioning said switch to accept input from said surgical bipolar generator and positioning said switch to accept input from said electrical nerve stimulator.

* * * * *